United States Patent [19]

Wade et al.

[11] 4,140,693
[45] Feb. 20, 1979

[54] SUBSTITUTED 2,3-DIHYDRO-1,2,4-TRIAZOLO [4,3-b][1,2]BENZISOTHIAZOL-3-AMINE, 5,5, DIOXIDES

[75] Inventors: Peter C. Wade, Pennington, N.J.; B. Richard Vogt, Yardley, Pa.; Thomas P. Kissick, Princeton, N.J.

[73] Assignee: E. R. Squibb & Sons, Inc., Princeton, N.J.

[21] Appl. No.: 875,021

[22] Filed: Feb. 3, 1978

[51] Int. Cl.² .................................... C07D 275/06
[52] U.S. Cl. ............................ 260/304 A; 546/199; 260/326.82; 544/135; 544/369; 424/248.51; 424/250; 424/256; 424/270
[58] Field of Search ................................. 260/304 A Primary Examiner—Donald G. Daus
Assistant Examiner—Lisa Jones
Attorney, Agent, or Firm—Lawrence S. Levinson; Merle J. Smith

[57] ABSTRACT

2,3-Dihydro-1,2,4-triazolo[4,3-b][1,2]benzisothiazol-3-amine, 5,5-dioxides having the formula

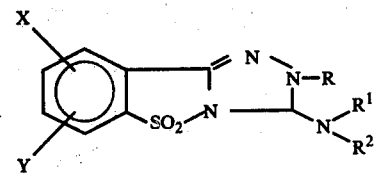

and salts thereof are new compounds which are useful as anti-inflammatory agents.

10 Claims, No Drawings

SUBSTITUTED 2,3-DIHYDRO-1,2,4-TRIAZOLO[4,3-b][1,2]BENZISOTHIAZOL-3-AMINE, 5,5, DIOXIDES

SUMMARY OF THE INVENTION

This invention relates to new 2,3-dihydro-1,2,4-triazolo[4,3-b][1,2]benzisothiazol-3-amine, 5,5-dioxides which have the general formula

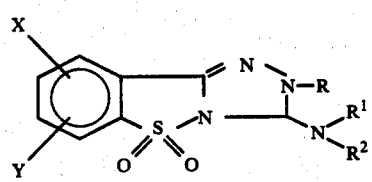

and to acid addition salts thereof; wherein

X is hydrogen, halogen, lower alkyl, lower alkoxy or nitro;

Y is hydrogen, lower alkoxy or halogen;

R is hydrogen, lower alkanoyl, benzoyl or substituted benzoyl wherein the benzoyl bears a halogen, lower alkyl, lower alkoxy or nitro group on the phenyl ring;

$R^1$ and $R^2$ each is lower alkyl or $R^1$ and $R^2$ together with the nitrogen form a 5- or 6-membered heterocycle of the group consisting of pyrrolidino, morpholino, thiamorpholino, piperidino or N-lower alkyl piperazino.

DETAILED DESCRIPTION

The lower alkyl groups represented by the symbols are straight or branched chain aliphatic hydrocarbon radicals having up to 7 carbon atoms, for example, methyl, ethyl, propyl, isopropyl, butyl, isobutyl, t-butyl and the like. The $C_1$–$C_4$ and especially the $C_1$–$C_3$ groups are preferred.

The lower alkoxy groups are also similar groups having up to 7 carbons like methoxy, ethoxy, propoxy, isopropoxy, butoxy, isobutoxy, t-butoxy, etc. The $C_1$–$C_4$ and especially $C_1$–$C_3$ groups are similarly preferred.

The halogens are the four common halogens, chlorine and bromine being preferred in that order.

When Y is other than hydrogen, X represents the same substituent as Y.

The amino groups

wherein $R^1$ and $R^2$ each represents lower alkyl, include di-lower alkylamino groups like dimethylamino, diethylamino, methylethylamino, dipropylamino, dibutylamino and the like (preferably, but not necessarily, both lower alkyl groups are the same in a given compound). $R^1$ and $R^2$ can also join with the nitrogen to form one of the 5- or 6-membered heterocyclic radicals pyrrolidino, morpholino, thiamorpholino, piperidino or N-lower alkyl piperazino, e.g., N-methylpiperazino.

The acyl radicals represented by R are the acyl radicals of the lower fatty acids having up to eight carbons, i.e.,

wherein $R^3$ is lower alkyl of the type described above, for example, acetyl, propanoyl, butanoyl, t-butanoyl and the like. Those having up to four carbons are preferred, especially acetyl. The acyl radicals represented by R are also benzoyl and mono-substituted benzoyl radicals, i.e.,

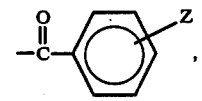

wherein Z has the same meaning as X, including, for example, benzoyl, p-chlorobenzoyl, o-chlorobenzoyl, m-chlorobenzoyl, p-bromobenzoyl, o-bromobenzoyl, m-bromobenzoyl, p-methylbenzoyl, p-methoxybenzoyl, m-ethoxybenzoyl, p-nitrobenzoyl, etc.

The preferred compounds of formula I are those wherein X and Y are both hydrogen; R is hydrogen, benzoyl or lower alkanoyl, particularly up to $C_4$ lower alkanoyl and especially acetyl; and

is di-lower alkylamino, particularly wherein the lower alkyl groups have up to 4 carbons and especially dimethylamino.

The products of this invention are produced by reacting a 3-hydrazino-1,2-benzisothiazole 1,1-dioxide having the formula

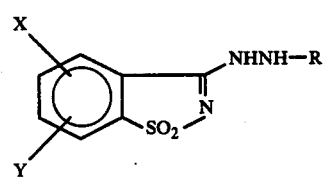

with a formamide of the formula

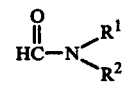

in the presence of a phosphorus oxyhalide like phosphorus oxychloride or phosphorus oxybromide.

The starting materials of formula II are produced from saccharin or a substituted saccharin which has the formula

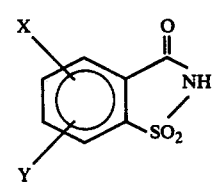

first, by reaction with thionyl chloride in an inert organic solvent like dioxane in the presence of dimethylformamide catalyst.

The product of this reaction is a compound of the formula

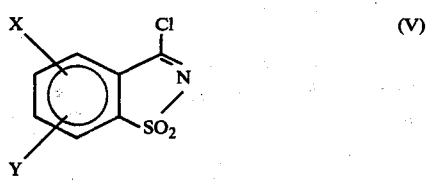

When R in the desired product of formula I is hydrogen, the intermediate of formula V is preferably converted to its derivative having the formula

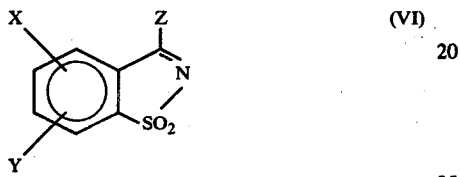

wherein Z is lower alkoxy or lower alkylthio, by reaction with an excess of alcohol or thiol ZH in a solvent such as acetone, e.g., at reflux temperature. The ether or thioether of formula VI is then converted with hydrazine, e.g., in methanol at about reflux temperature, to the desired starting material of formula II (R=H).

When R in the desired product of formula I is an acyl radical, the preferred method is to react the chloro compound of formula V directly with an acyl hydrazine of the formula

wherein $R^1$ is lower alkyl, phenyl or substituted phenyl, e.g., by refluxing in toluene.

The compounds of formula I form salts which are also part of this invention. The salts include acid addition salts, particularly the non-toxic, physiologically acceptable members. The bases of formula I form salts by reaction with an equivalent or more of a variety of inorganic and organic acids providing acid addition salts including, for example, hydrohalides (especially hydrochloride and hydrobromide), sulfate, nitrate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating the product, e.g., by forming and precipitating the salt (which is not necessarily nontoxic) in an appropriate medium in which the salt is insoluble, then after separation of the salt, neutralizing with a base such as barium hydroxide or sodium hydroxide, to obtain the free base of formula I. Other salts can then be formed from the free base by reaction with an equivalent or more of acid.

The new compounds of this invention have anti-inflammatory properties and are useful as anti-inflammatory agents, for example, to reduce local inflammatory conditions such as those of an edematous nature or resulting from proliferation of connective tissue in various mammalian species such as rats, mice, dogs and the like when given orally or parenterally in dosages of about 5 to 150 mg/kg/day, preferably 10 to 75 mg/kg/day, in single or 2 to 4 divided doses, as indicated by the Mouse Active Arthus assay. The active substance can be utilized in compositions such as tablets, capsules, solutions or suspensions containing up to about 300 mg. per unit of dosage of a compound or mixture of compounds of formula I or physiologically acceptable acid addition salt thereof. They are compounded in conventional manner with a physiologically acceptable vehicle or carrier, excipient, binder, preservative, stabilizer, flavor, etc. as called for by accepted pharmaceutical practice.

The following examples are illustrative of the invention and constitute preferred embodiments. They also serve as models for the preparation of other members of the group. All temperatures are in degrees Celsius.

EXAMPLE 1

2,3-Dihydro-N,N-dimethyl-1,2,4-triazolo[4,3-b][1,2]benzisothiazol-3-amine 5,5-dioxide (a) 100 g (545 mM) of benzisothiazole 1,1-dioxide, 100 ml. of thionyl chloride, 4 ml. of dimethylformamide (catalyst), and 400 ml. of dioxane are refluxed overnight. Thionyl chloride (50 ml.) and dimethylformamide (1 ml.) are added to the reaction mixture which is again refluxed overnight. The reaction mixture is evaporated to dryness and the residue recrystallized from toluene to obtain 73.4 g. of 3-chloro-1,2-benzisothiazole-1,1-dioxide, m.p. 140°–145°.

(b) 12.0 g (59.6 mM) of 3-chloro-1,2-benzisothiazole, 1,1-dioxide are dissolved in 200 ml. of acetone. Ethanol (2 equivalents) are added and the mixture is refluxed for 1 hour and evaporated to dryness. The residue is digested with ethanol and filtered to yield 9.5 g. of the product, 3-ethoxy-1,2-benzisothiazole, 1,1-dioxide, m.p. 210°–211°.

(c) 13.8 g (408 mM) of hydrazine (95%) is added to 86.3 g (408 mM) of 3-ethoxy-1,2-benzisothiazole, 1,1-dioxide in 2 liters of refluxing methanol. The mixture is refluxed for 1 hour and stirred at room temperature for two days. The product, 3-hydrazino-1,2-benzisothiazole, 1,1-dioxide, is filtered out and dried at 80°/vacuum: yield 70.4 g m.p. 250°–251°.

(d) 20.0 g. (101.5 mM) of 3-hydrazino-1,2-benzisothiazole, 1,1-dioxide are taken up in 500 ml. of dimethylformamide. Phosphorus oxychloride (9 ml.) is added dropwise to the stirred solution. After 1 hour, 300 ml. of ether is added, the resulting mixture is stirred for 30 minutes and the white precipitate is filtered and washed with 50% ether/dimethylformamide. The precipitate is stirred as a suspension in 300 ml. of ethanol and triethylamine is added dropwise until the solid dissolves and the solution is neutral to pH paper. Yellow solid 2,3-dihydro-N,N-dimethyl-1,2,4-triazolo[4,3-b] 1,2]benzisothiazol-3-amine 5,5-dioxide crystallizes out overnight and is filtered, washed with ethanol, and dried at 80°/vacuum; yield 4.85 g m.p. 210°–211°.

The hydrochloride salt is prepared by dissolving the above product in ethanol and adding a solution of ethanol-HCl containing 1.1 equivalents of the HCl then precipitating the salt by the addition of ether.

EXAMPLE 2

2-Benzoyl-2,3-dihydro-N,N-dimethyl-1,2,4-triazolo[4,3-b][1,2]-benzisothiazol-3-amine, 5,5-dioxide (a) 6.0 g. (29.8 mM) of 3-chloro-1,2-benzisothiazole, 1,1-dioxide and 4.05 g (29.8 mM) of benzoylhydrazine are refluxed in 200 ml. toluene for 1 hour. After cooling to room temperature, the precipitate is filtered off, and dissolved in 400 ml. of ethanol and 100 ml. water containing 5 ml. triethylamine. The product, benzoic acid, 2-(1,1-dioxo-1,2-benzisothiazol-3-yl)hydrazide, is precipitated by the addition of concentrated HCl (to pH 7), filtered, washed with water and alcohol, and dried at 80°/vacuum for 5 hours; yield: 6.25 g, m.p. 289°–290°.

(b) 6.7 g (22.3 mM) of benzoic acid, 2-(1,1-dioxo-1,2-benzisothiazol-3-yl)hydrazide are dissolved in 200 ml. of dimethylformamide and 25 ml. of phosphorus oxychloride are added. After 3 hours, the solution is poured into 1.5 liters of water. Crystals form after stirring for a few minutes. After 2 hours, the crystals are filtered out, washed with water, and the product, 2-benzoyl-2,3-dihydro-N,N-dimethyl-1,2,4-triazolo[4,3-b][1,2]benzisothiazol-3-amine, 5,5-dioxide is recrystallized from a mixture of 50 ml. ethanol, 200 ml. water; yield 5.6 g, m.p. 155°–156°.

The following additional compounds of formula I having the substituents in the table are produced according to the procedure of Example 1 or Example 2 by substituting the appropriately unsubstituted or substituted compounds of formulas II and III, having the substituents indicated in the table:

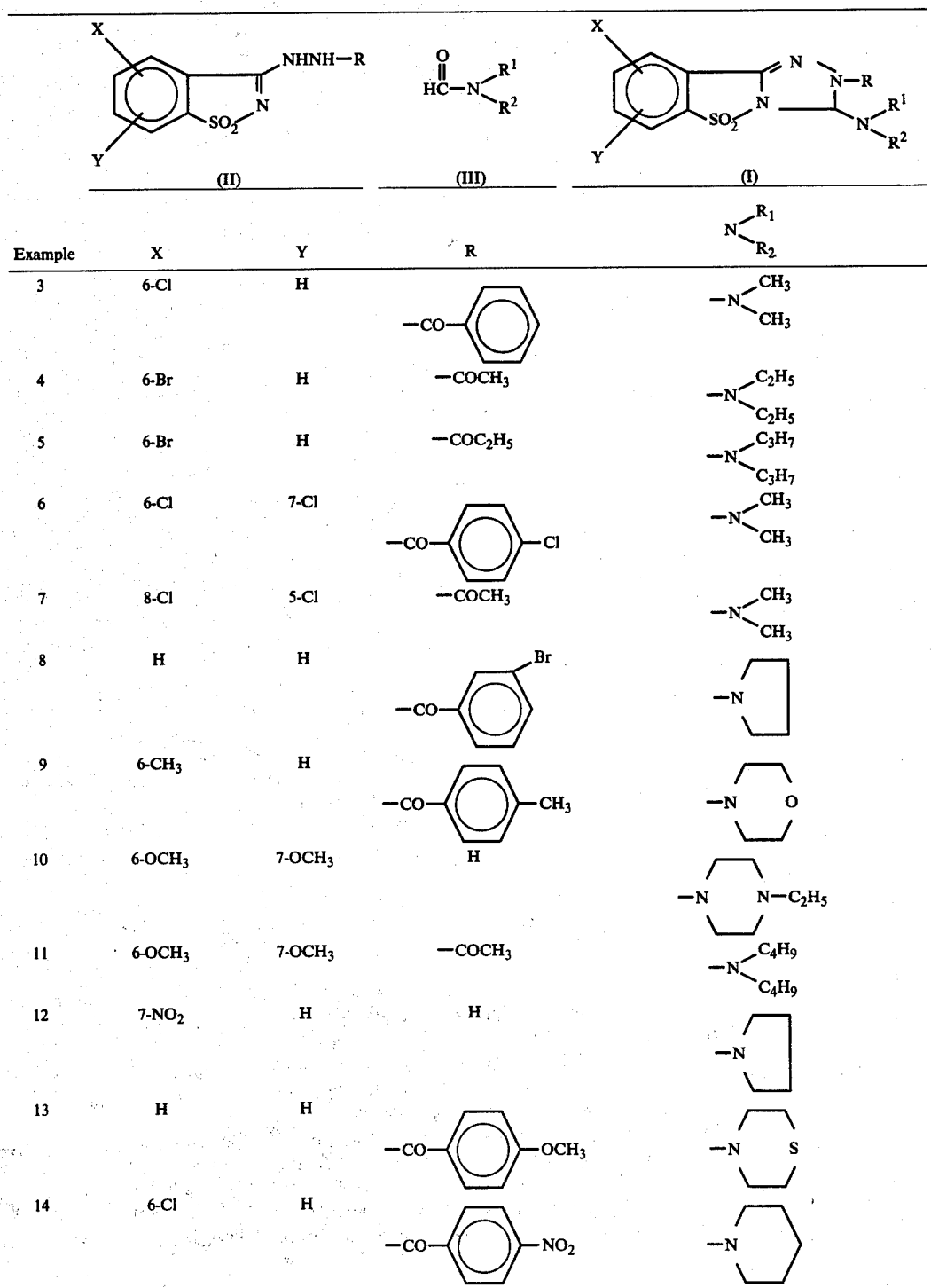

-continued

| | (II) 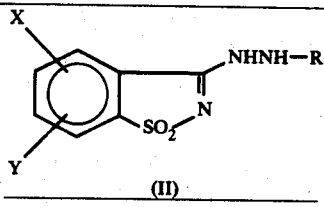 | (III) 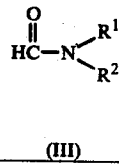 | (I) 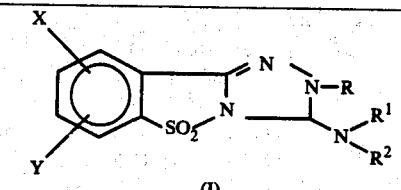 |
|---|---|---|---|
| Example | X | Y | R | NR₁R₂ |
| 15 | H | H | 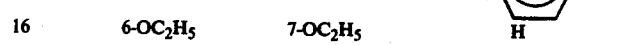 -CO-C₆H₄-CH₃ | 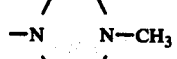 -N(piperazine)N-CH₃ |
| 16 | 6-OC₂H₅ | 7-OC₂H₅ | H | 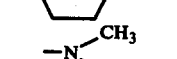 -N(piperazine)N-CH₃ |
| 17 | 7-OCH₃ | 8-OCH₃ | —COC₃H₇ | 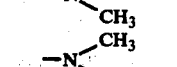 —N(CH₃)₂ |
| 18 | H | H | —COCH₃ | 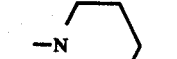 —N(CH₃)₂ |
| 19 | H | H |  —CO-C₆H₅ | 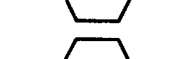 —N(piperidine) |
| 20 | H | H | —COCH₃ |  —N(piperidine) |
| 21 | H | H | H | 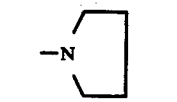 —N(piperidine) |
| 22 | H | H | H | —N(pyrrolidine) |

What is claimed is:
1. A compound of the formula

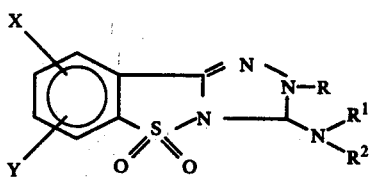

and physiologically acceptable acid addition salts thereof, wherein
X is hydrogen, halogen, lower alkyl, lower alkoxy or nitro;
Y is hydrogen, lower alkoxy or halogen, X being the same as Y when Y is other than hydrogen;
R is hydrogen, lower alkanoyl, benzoyl or substituted benzoyl wherein the benzoyl bears a halogen, lower alkyl, lower alkoxy or nitro group on the phenyl ring;
R¹ and R² each is lower alkyl.

2. A compound as in claim 1 wherein X and Y each is hydrogen.
3. A compound as in claim 1 wherein R is hydrogen.
4. A compound as in claim 1 wherein R is lower alkanoyl.
5. A compound as in claim 1 wherein R is

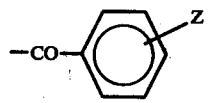

wherein Z is hydrogen, halogen, lower alkyl, lower alkoxy or nitro.
6. A compound as in claim 1 wherein R is benzoyl.
7. A compound as in claim 1 wherein R¹ and R² each is lower alkyl.
8. A compound as in claim 2 wherein R is hydrogen and R¹ and R² each is methyl.
9. A compound as in claim 2 wherein R is benzoyl and R¹ and R² each is methyl.
10. A compound as in claim 2 wherein R is acetyl and R¹ and R² each is methyl.